United States Patent
Kondis et al.

(10) Patent No.: US 11,129,708 B2
(45) Date of Patent: Sep. 28, 2021

(54) BIREFRINGENT INTRAOCULAR LENS

(71) Applicant: RxSight, Inc., Aliso Viejo, CA (US)

(72) Inventors: John Kondis, Irvine, CA (US); Ilya Goldshleger, Ladera Ranch, CA (US)

(73) Assignee: RxSight, Inc., Aliso Viejo, CA (US)

( * ) Notice: Subject to any disclaimer, the term of this patent is extended or adjusted under 35 U.S.C. 154(b) by 0 days.

(21) Appl. No.: 15/665,410

(22) Filed: Jul. 31, 2017

(65) Prior Publication Data

US 2019/0029809 A1 Jan. 31, 2019

(51) Int. Cl.
| | |
|---|---|
| *A61F 2/16* | (2006.01) |
| *A61L 27/44* | (2006.01) |
| *A61L 27/50* | (2006.01) |
| *G02B 1/08* | (2006.01) |

(52) U.S. Cl.
CPC .......... *A61F 2/1627* (2013.01); *A61F 2/1618* (2013.01); *A61L 27/44* (2013.01); *A61L 27/50* (2013.01); *G02B 1/08* (2013.01); *A61F 2002/1681* (2013.01); *A61L 2430/16* (2013.01)

(58) Field of Classification Search
None
See application file for complete search history.

(56) References Cited

U.S. PATENT DOCUMENTS

| | | | | |
|---|---|---|---|---|
| 5,073,021 A | * | 12/1991 | Marron | G02C 7/06 351/159.41 |
| 5,142,411 A | | 8/1992 | Fiala | |
| 5,410,375 A | | 4/1995 | Fiala | |
| 5,895,422 A | * | 4/1999 | Hauber | A61F 2/1613 351/159.11 |
| 6,250,757 B1 | | 6/2001 | Roffman et al. | |

(Continued)

FOREIGN PATENT DOCUMENTS

WO    WO 2014/058315 A1    4/2014

*Primary Examiner* — Leslie Lopez

(57) ABSTRACT

A multifocal intraocular lens (MF-IOL) includes a circularly birefringent material with a right-handed index of refraction $n_R$ for a light with a right-handed polarization, and a left-handed index of refraction $n_L$ for a light with a left-handed polarization; and haptics, to position the multifocal intraocular lens inside a capsule of an eye; wherein the multifocal intraocular lens has a right-handed optical power $D_R$ for the light with the right-handed polarization, and a left-handed optical power $D_L$ for the light with the left-handed polarization, wherein $D_L/D_R=(n_L-1)/(n_R-1)$. Some variations of the MF-IOL include stimulus-orientable optically anisotropic constituents. Some classes of the MF-IOL include a self-assembling optically anisotropic compound. A corresponding method of making a MF-IOL is comprising providing stimulus-orientable optically anisotropic constituents as part of an intraocular lens; orienting the optically anisotropic constituents by applying a non-stretching stimulus; and locking-in the oriented optically anisotropic constituents to form the multifocal intraocular lens.

5 Claims, 10 Drawing Sheets

(56) References Cited

U.S. PATENT DOCUMENTS

| | | | |
|---|---|---|---|
| 2007/0021831 A1* | 1/2007 | Clarke | A61F 2/1601 623/6.13 |
| 2008/0208335 A1* | 8/2008 | Blum | A61F 2/1616 623/6.22 |
| 2010/0076554 A1 | 3/2010 | Sandstedt et al. | |
| 2010/0094412 A1 | 4/2010 | Wensrich | |
| 2015/0029424 A1 | 1/2015 | Gordon et al. | |
| 2016/0339657 A1 | 11/2016 | Grubbs et al. | |

\* cited by examiner

BIREFRINGENT INTRAOCULAR LENS

TECHNICAL FIELD

This invention relates to intraocular lenses, and in more detail, to multi-focal intraocular lenses with birefringence.

BACKGROUND

The techniques of cataract surgery are experiencing continuous, impressive progress. Subsequent generations of phacoemulsification platforms and newly invented surgical lasers keep increasing the precision of the placement of intraocular lenses (IOLs), and keep reducing the unwanted medical outcomes.

One area of continued development and exploration is presbyopia, the condition of the aging eye gradually losing its ability to adapt and focus on targets at different distances. Various IOL designs have been proposed to alleviate presbyopia. These include multifocal IOLs and their variants, which focus spatially separate portions of the incoming light beam to different focal depths. A typical multifocal IOL design is to form a central disc in the IOL with an optical power adapted for near vision, and an annular region in the IOL with an optical power adapted to distance vision. Another class of presbyopia IOLs addresses the same challenge by forming diffractive structures that focus the light into multiple focal planes. However, after many years of development, these presbyopia IOLs still have limitations and only fractional market acceptance. Therefore, there is a persistent medical need to explore alternative approaches and designs for presbyopia IOLs.

SUMMARY

The above-described needs are addressed by embodiments of a multifocal intraocular lens that comprises a circularly birefringent material with a right-handed index of refraction $n_R$ for a light with a right-handed polarization, and a left-handed index of refraction $n_L$ for a light with a left-handed polarization; and haptics, to position the multifocal intraocular lens inside a capsule of an eye; wherein the multifocal intraocular lens has a right-handed optical power $D_R$ for the light with the right-handed polarization, and a left-handed optical power $D_L$ for the light with the left-handed polarization, wherein: $D_L/D_R=(n_L-1)/(n_R-1)$.

In some embodiments, a multifocal intraocular lens is comprising stimulus-orientable optically anisotropic constituents, adapted to modify the multifocal intraocular lens to have an ordinary index of refraction $n_o$ for a light with an ordinary polarization, and an extraordinary index of refraction $n_e$ for a light with an extraordinary polarization; the multifocal intraocular lens having an ordinary optical power $D_o$ for the light with the ordinary polarization, and an extraordinary optical power $D_e$ for the light with the extraordinary polarization, wherein $D_e/D_o=(n_e-1)/(n_o-1)$; and haptics, to position the multifocal intraocular lens inside a capsule of an eye.

In some embodiments, multifocal intraocular lens is comprising self-assembling optically anisotropic compound; adapted to modify the multifocal intraocular lens to have an ordinary index of refraction $n_o$ for an ordinary light component; an extraordinary index of refraction $n_e$ for an extraordinary light component; an ordinary optical power $D_o$ for the ordinary light component; and an extraordinary optical power $D_e$ for the extraordinary light component, wherein $D_e/D_o=(n_e-1)/(n_o-1)$; and haptics, to position the multifocal intraocular lens inside an eye.

In some embodiments, a method of making a multifocal intraocular lens is comprising providing stimulus-orientable optically anisotropic constituents as part of an intraocular lens; orienting the optically anisotropic constituents by applying a non-stretching stimulus; and locking-in the oriented optically anisotropic constituents to form the multifocal intraocular lens.

DETAILED DESCRIPTION

As mentioned in the background section, the two main existing classes of intraocular lenses that create multiple focal planes are (1) multifocal IOLs, and the closely related spherical aberration IOLs and zonal IOLs; and (2) diffractive IOLs. Both IOL classes have significant drawbacks.

(1) Multifocal IOLs and spherical aberration (SA) IOLs both provide an Extended Depth Of Focus (EDOF), in order to alleviate presbyopia. Over time, the eye develops the capability of concentrating on the image that is brought into sharp focus on the retina by such EDOF IOLs. However, IOLs in this class exhibit a notable pupil size dependence of the visual acuity (VA), because they have a strongly pupil-dependent optimal focal distance. For example, with positive SA, distance vision during daylight may be acceptable, but this is achieved at the cost of a significantly reduced distance VA at night, when the pupil is wider. Alternatively, a negative SA can deliver a better distance VA at night, but at the expense of a worse distance VA during bright daylight conditions. These tradeoffs can become so disadvantageous that they create binocular inhibition, when the difference in vision between the two eyes becomes so great that vision with both eyes open can be worse than when only one eye is viewing.

(2) The class of diffractive IOLs create multifocality, or spherical aberrations, by an intricate diffractive pattern of edges and troughs, building on the interference patterns of the refracted light. However, these diffractive patterns of these diffractive IOLs tend to create ghosting, scattering and halos. These types of undesirable light-scattering can be managed to some degree by limiting the spatial frequency content of the diffractive profiles, or by limiting the transmitted wavelength band itself by absorbing the blue component of the light. However, this light-scattering management comes at the cost of increased aberrations of the zero-order focus, and other issues related to blocking blue light from the patient's retina.

Embodiments of Intraocular Lenses described in this patent document can provide an Extended Depth Of Focus, while avoiding and overcoming the discussed disadvantages (1)-(2).

Figure 1A:
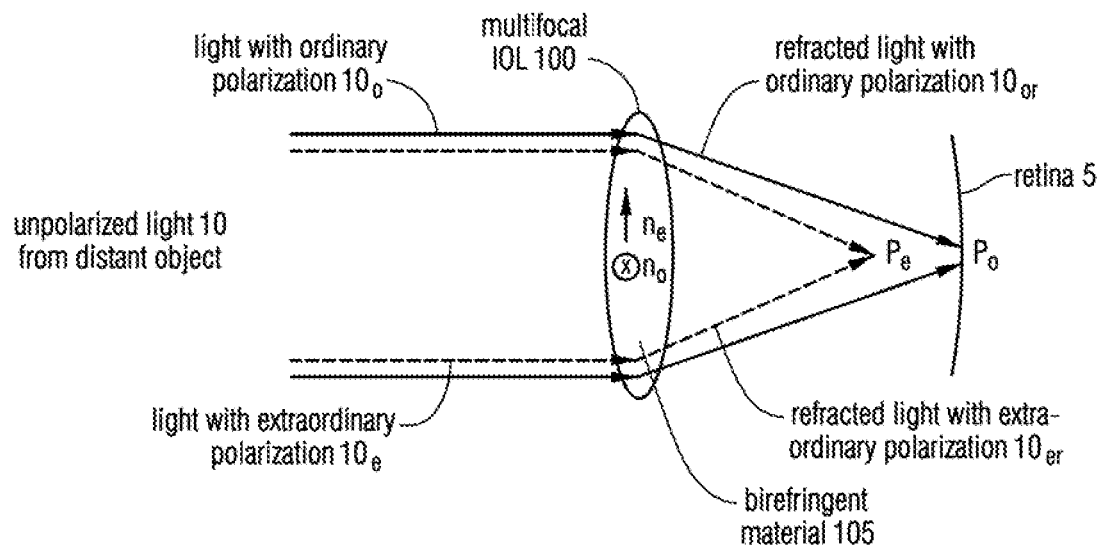
FIGS. 1A-B illustrate the propagation of the light in a multifocal IOL with a birefringent material.
Figure 1B:
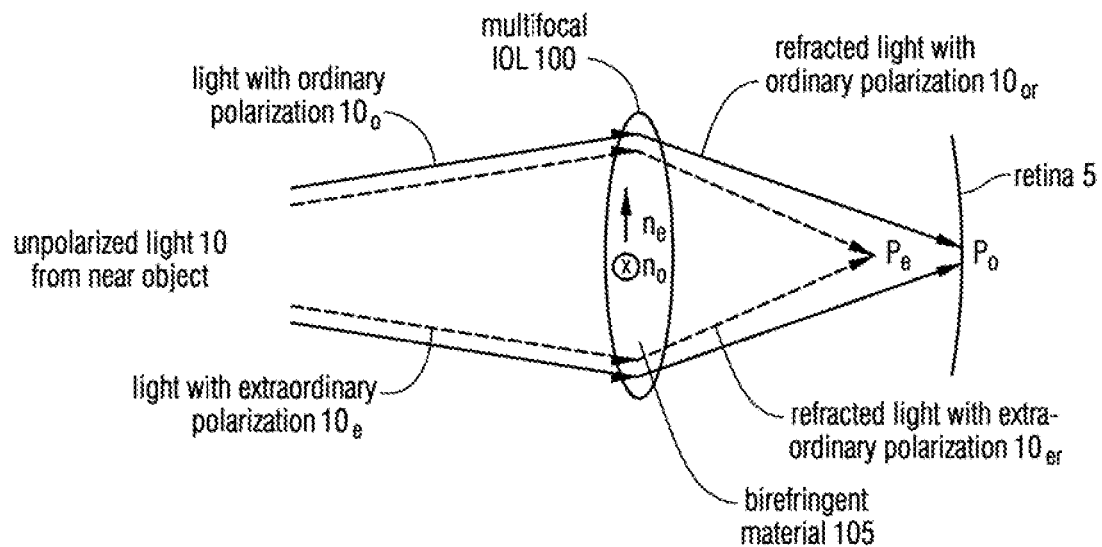

FIGS. 1A-B illustrate a multifocal intraocular lens 100, comprising a birefringent material 105 that has an ordinary index of refraction $n_o$ for a light with an ordinary polarization $10_o$, and a different, extraordinary index of refraction $n_e$ for a light with an extraordinary polarization $10_e$. Therefore, the multifocal IOL 100, or MF-IOL 100, refracts the light with the ordinary polarization $10_o$ as a refracted light with ordinary polarization $10_{or}$, and the light with the extraordinary polarization $10_e$ differently, as a refracted light with extraordinary polarization $10_{er}$. Accordingly, embodiments of the MF-IOL 100 have an ordinary optical power $D_o$ for the light with the ordinary polarization $10_o$, and a different, extraordinary optical power $D_e$ for the light with the extraordinary polarization $10_e$. This optical phenomenon is often termed "birefringence". The two optical powers are related to each other with a suitable precision as:

$$D_e/D_o=(n_e-1)/(n_o-1) \quad (1)$$

The orientations of a plane of ordinary polarization and a plane of extraordinary polarization are typically determined by an optical anisotropy of the birefringent material 105. In some embodiments, the ordinary and extraordinary polarizations can be linear, circular, or elliptical, and can be defined by well-known corresponding geometric indicators other than polarization planes.

An unpolarized light 10 typically includes light rays with all possible polarizations, and therefore the unpolarized light 10 typically includes light with the ordinary polarization $10_o$, as well as light with extraordinary polarization $10_e$.

FIG. 1A illustrates that when the unpolarized light 10 from a distant object is incident on the MF-IOL 100, essentially as parallel rays, including lights $10_o$ and $10_e$, the unique optical characteristics of the birefringent material 105 focus the refracted light $10_{or}$ into point $P_o$ on a retina 5, and the refracted light $10_{er}$ into point $P_e$ proximal to the retina 5.

FIG. 1B illustrates that when the unpolarized light 10 from a near object is incident on the MF-IOL 100, essentially as moderately divergent rays including lights $10_o$ and $10_e$, the unique optical characteristics of the birefringent material 105 focus the refracted light $10_{or}$ into point $P_o$ distal to the retina 5, and the refracted light $10_{er}$ into point $P_e$ on the retina 5. The depth range, swept by $P_e$ and $P_o$ for target distances ranging from infinity to very near targets, defines the extended depth of focus EDOF. Therefore, MF-IOLs 100 with the birefringent material 105 provide an extended depth of focus and thus are one approach promising to manage and to counteract presbyopia.

In embodiments of the MF-IOL 100, the birefringent material 105 can be selected from a group that has an ordinary index of refraction $n_o$ and an extraordinary index of refraction $n_e$ such that the induced ordinary optical power $D_o$ and the extraordinary optical power $D_e$ cover the needs of presbyopia patients. In some embodiments, this means that a difference between $D_o$ and $D_e$ can be in the range of 0.5-3 diopters. In other embodiments, this range can be 1-2 diopters.

In certain embodiments of a MF-IOL 100, having a biconvex lens with equal distal and proximal radii of curvatures R, the indices of refraction and the corresponding optical powers are related as:

$$(n_e-n_o)=(D_e-D_o)*R/2 \quad (2)$$

Typical IOLs have an optical power in the range of 15-25 diopters, and a radius of curvature in the range of 5-15 mm. Thus, in an illustrative example, for an IOL with optical power of 20 diopters, and a radius of 10 mm, an optical power difference of 1 diopter can be delivered by an index of refraction difference of $\Delta n=n_e-n_o=0.005$. Such small differences between the ordinary and extraordinary indices of refraction are known to occur in various birefringent materials 105. In fact, $\Delta n$ values that are 10-40 times greater than 0.005 are known to occur in bulk birefringent materials. Accordingly, embodiments of the MF-IOL 100 can be well-adapted to focus some of the incident light rays both from distant and from near objects onto the retina 5, and thus perform as bifocal, or EDOF, IOLs.

Such MF-IOLs 100 avoid the above two disadvantages of existing classes of presbyopia IOLs as follows. (1) Since the entire cross section of the MF-IOL 100 participates in refracting the light with the ordinary polarization $10_o$, as well as the light with the extraordinary polarization $10_e$, the Visual Acuity exhibits only a very limited dependence on the pupil diameter. This is in contrast to existing multifocal IOLs, which focus the light from the distant objects, or sometimes the near objects, only with their peripheric annulus, whose surface area is reduced much more dramatically when the pupil narrows. (2) Since the MF-IOL 100 delivers its EDOF without diffractive patterns, defined by grooves and edges, the MF-OL 100 does not generate halos and glares. This is in contrast to diffractive IOLs that rely on diffractive grove and edge patterns to deliver the EDOF. For all the above described reasons, embodiments of the MF-IOL 100 offer marked improvements and superior visual acuity over existing IOLs.

Figure 2:
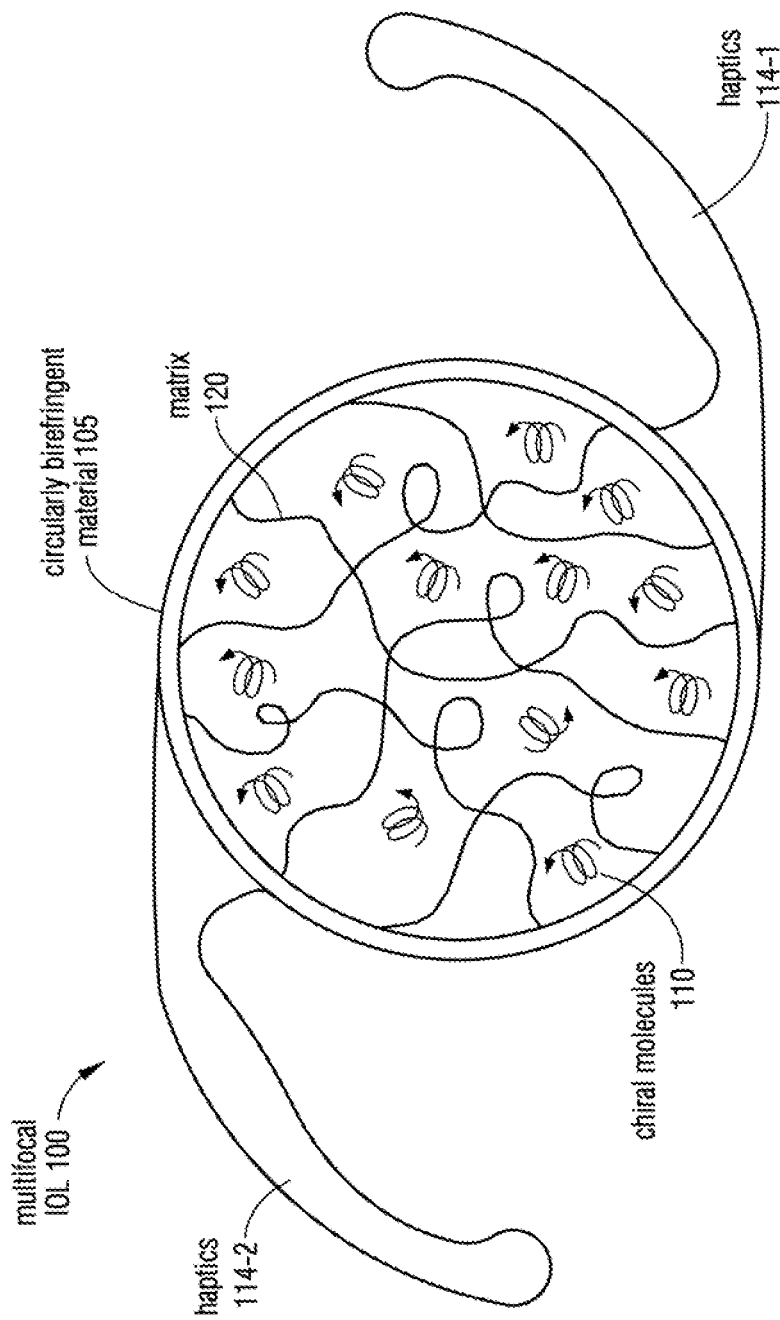
FIG. 2 illustrates a birefringent multifocal IOL with chiral molecules.

FIG. 2 illustrates an embodiment of a multifocal intraocular lens 100, or MF-IOL 100 that includes a circularly birefringent material 105 with a right-handed index of refraction $n_R$ for a light with a right-handed polarization, and a left-handed index of refraction $n_L$ for a light with a left-handed polarization; and haptics 114-1 and 114-2, cumulatively haptics 114, to position the multifocal intraocular lens 100 inside a capsule of an eye. The MF-IOL 100 can have a right-handed optical power $D_R$ for the light with the right-handed polarization, and a left-handed optical power $D_L$ for the light with the left-handed polarization, where:

$$D_L/D_R=(n_L-1)/(n_R-1) \quad (3)$$

Circularly birefringent MF-IOLs can deliver functionalities different from linearly birefringent MF-IOLs. One of these differences is that light reflected from some flat surfaces tends to be polarized in the plane of the reflecting surface. A well-known example is the sunlight reflected from water. In such situations, a linearly birefringent MF-IOL could exhibit a Visual Acuity that strongly depends on the orientation of the polarization planes of the MF-IOL relative to the reflecting surface as the patient is moving or rotating his/her eyes. This could be quite inconvenient. In contrast, MF-IOLs with circular polarization do not exhibit such disorienting orientation dependence of the Visual Acuity.

In some MF-IOLs 100, the circularly birefringent material 105 can include chiral molecules 110, embedded into a matrix 120, or host matrix 120. The matrix 120 can include monomers, macromers, and polymers. Typical examples of matrix materials include silicones and acrylates, the leading base materials of present day IOLs. Other, analogous materials can also be included in the matrix 120.

Figure 3A:
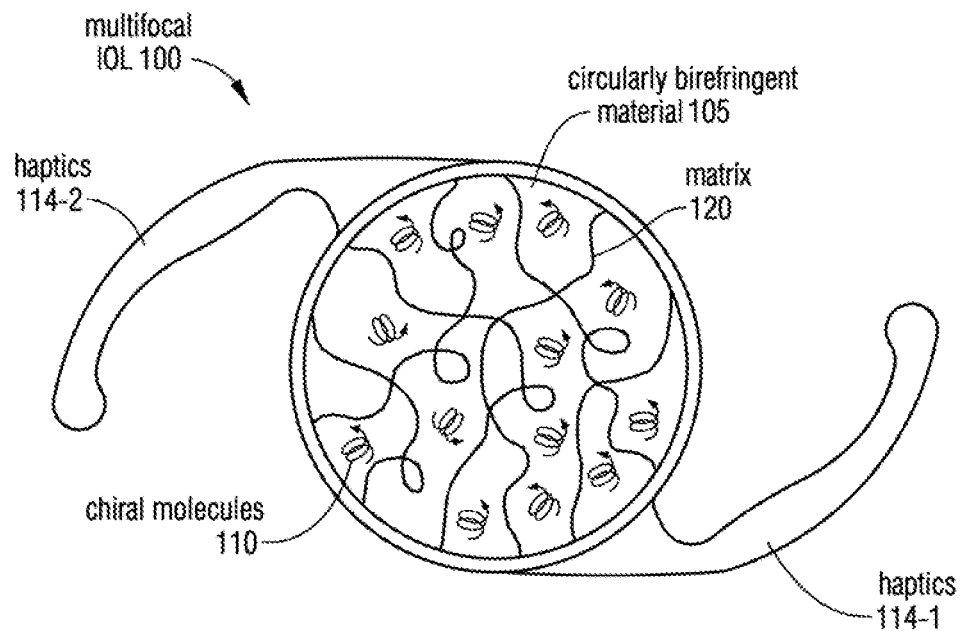
FIGS. 3A-B illustrate a circularly birefringent multifocal IOL with chiral molecules before and after alignment.
Figure 3B:
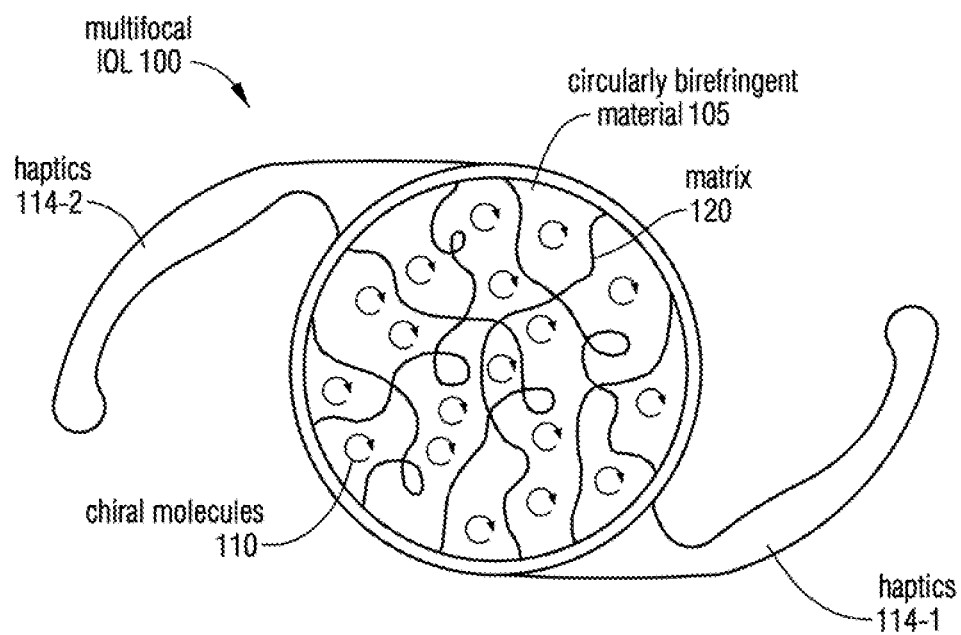

FIGS. 3A-B illustrate that the chiral molecules 110 can exhibit some degree of birefringence even if they are not aligned, and thus can extend the depth of focus. In some embodiments, such as in FIG. 3B, the chiral molecules 110 can be spatially aligned, and extend the depth of focus even more efficiently. In these embodiments, the chiral molecules 110 can be aligned axially instead of laterally in relation to the MF-IOL 100. Here, axial refers to alignment along a z axis, the direction of light propagation, normal to a major plane of the MF-IOL 100, and lateral refers to an alignment within the major plane of the MF-IOL 100.

In various embodiments of the MF-IOLs 100, the chiral molecules 110 can include a DNA, an optically active isomer of a sugar, a liquid crystal, a cholesteric molecule, a cholesteric liquid crystal, or a chiral molecule with circular birefringence.

Figure 4A:
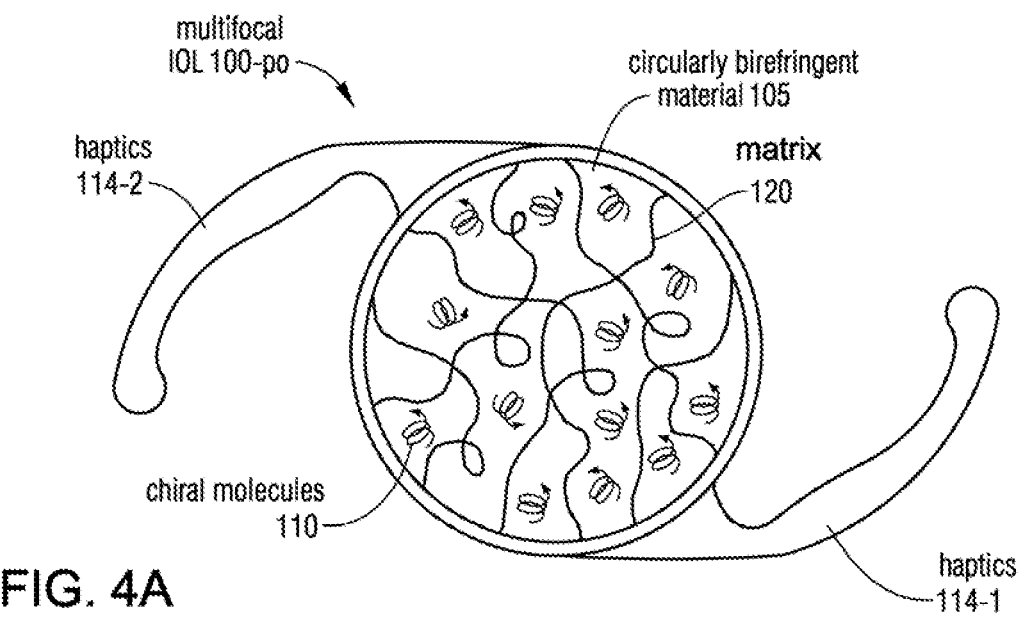
FIGS. 4A-C illustrate a circularly birefringent multifocal IOL with chiral molecules before alignment (FIG. 4A), the application of an aligning stimulus (FIG. 4B), and after alignment (FIG. 4C).
Figure 4B:
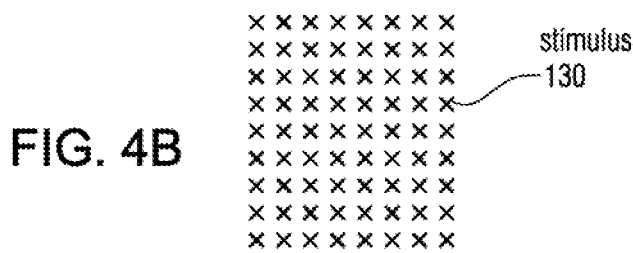
Figure 4C:
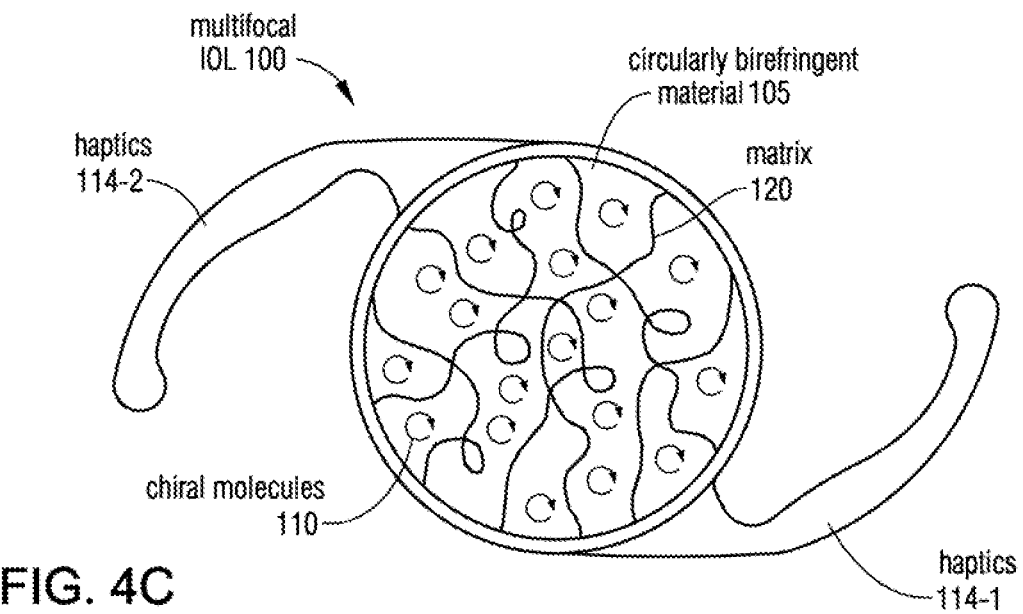

FIGS. 4A-C illustrate that in some MF-IOLs 100 the circularly birefringent material 105 that includes the chiral molecules 110 and the host matrix 120, can be stimulus adjustable. FIG. 4A shows an MF-IOL 100-po in a fabrication stage, where the "po" label indicates that the IOL is "prior to orientation" by a stimulus, when the chiral molecules 110 are not yet oriented by a stimulus. FIG. 4B symbolically represents an application of a stimulus 130. This stimulus 130 can be an application of an electric field, a magnetic field, a thermal gradient, or a chemical gradient; or an illumination with a linearly polarized light or a circularly polarized light, as detailed further below. The stimulus is directed in a manner to align the chiral molecules 110 axially. In the shown example, the stimulus electric field is applied axially (directed into the page) to align the chiral molecules 110. Finally, FIG. 4C illustrates that the chiral molecules 110 in the matrix 120 can be aligned and oriented axially as a result of the application of the stimulus 130, thus creating an embodiment of the MF-IOL 100 from the prior-to-orientation MF-IOL 100-po, where the chiral molecules 110 have not yet been oriented by the stimulus 130.

FIGS. 5A-D illustrate embodiments of the multifocal intraocular lens 100 that can include stimulus-orientable optically anisotropic constituents 210, adapted to modify the multifocal intraocular lens 100 to have an ordinary index of refraction $n_o$ for a light with an ordinary polarization, and an extraordinary index of refraction $n_e$ for a light with an extraordinary polarization; the multifocal intraocular lens 100 having an ordinary optical power $D_o$ for the light with the ordinary polarization, and an extraordinary optical power $D_e$ for the light with the extraordinary polarization, wherein: $D_e/D_o=(n_e-1)/(n_o-1)$. Furthermore, the MF-IOL 100 can again include haptics 114, to position the MF-IOL 100 inside a capsule of an eye.

In embodiments of the MF-IOL 100, the stimulus-orientable optically anisotropic constituents 210 can include a silicone macromer, a PMMA, an acrylate macromer, or any of the other analogous macromers that are widely used for manufacturing today's IOLs.

Figure 5A:
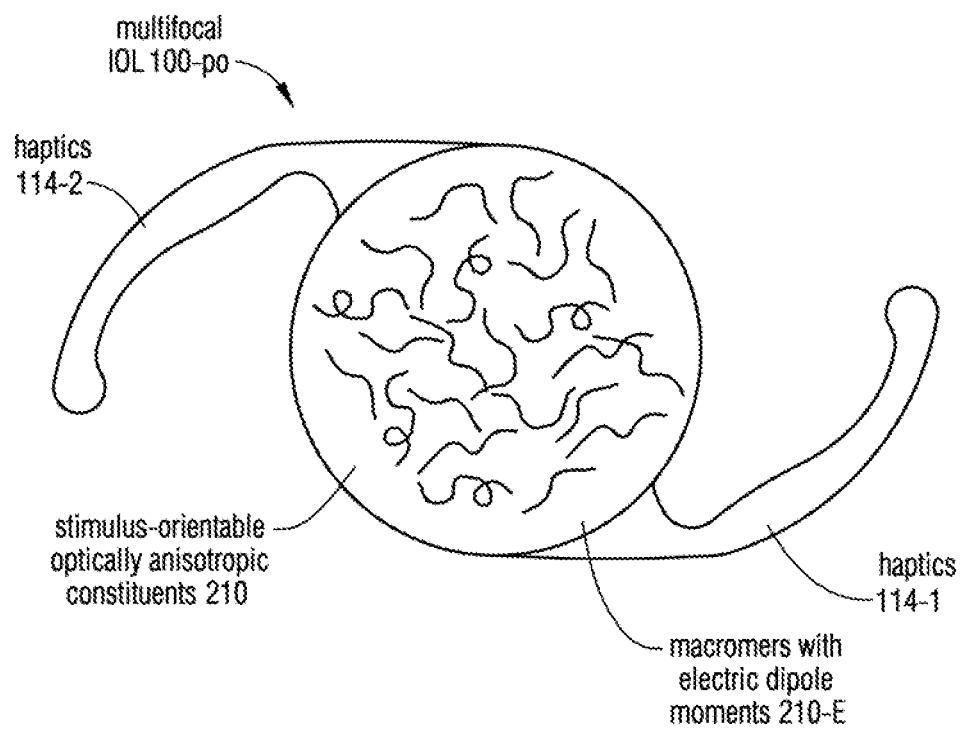
FIGS. 5A-D illustrate a multifocal IOL with stimulus-orientable optically anisotropic constituents before stimulus-induced orientation (FIG. 5A), the application of an orienting electric field stimulus (FIG. 5B), the oriented optically anisotropic constituents after the application of the orienting electric field stimulus (FIG. 5C), and the polymerized oriented optically anisotropic constituents in the MF-IOL (FIG. 5D).
Figure 5B:
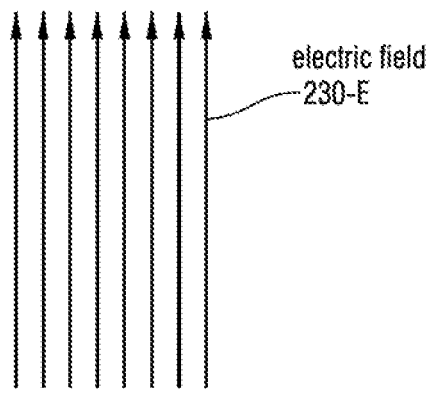

FIG. 5A shows the MF-IOL 100-po in a fabrication stage prior-to-orientation, when the stimulus-orientable optically anisotropic constituents 210 are pointing in random directions, not yet oriented by a stimulus. In the shown example, the stimulus-orientable optically anisotropic constituents 210 include macromers with electric dipole moments 210-E. As described below, there are numerous other types of stimulus-orientable optically anisotropic constituents 210. FIG. 5B shows symbolically the application of an external stimulus 230 to modify the multifocal intraocular lens 100, analogously to the stimulus 130. In the shown example, the stimulus 230 can be an electric field 230-E. An electric field 230-E can be applied to the MF-IOL 100, for example, by placing the MF-IOL 100 between the plates of a parallel plate capacitor and then charging the capacitor to a suitable voltage. As is well known, an electric field 230-E exerts a torque on molecules or macromers with an electric dipole moments 210-E. With the correct orientation of the electric field 230-E, the macromers with an electric dipole moments 210-E can be aligned to deliver the desired birefringence.

For MF-IOLs 100, where the ordinary and extraordinary polarizations are related to different linear polarizations with polarization planes, the electric field can be directed laterally, in the major plane of the MF-IOL 100. For the chiral embodiments of MF-IOL 100 in FIG. 3B, the electric field can be directed axially, perpendicular to the plane of the MF-IOL 100. Since the axial thickness of the MF-IOL 100 is much smaller than its lateral diameter, the stimulus electric field 230-E can be applied to the latter MF-IOLs 100 with the capacitor's electrodes much closer to each other. In such close-electrode capacitors, the same electric field can be induced with much lower voltages than in far-electrode capacitors, like the ones needed for a lateral alignment.

Figure 5C:
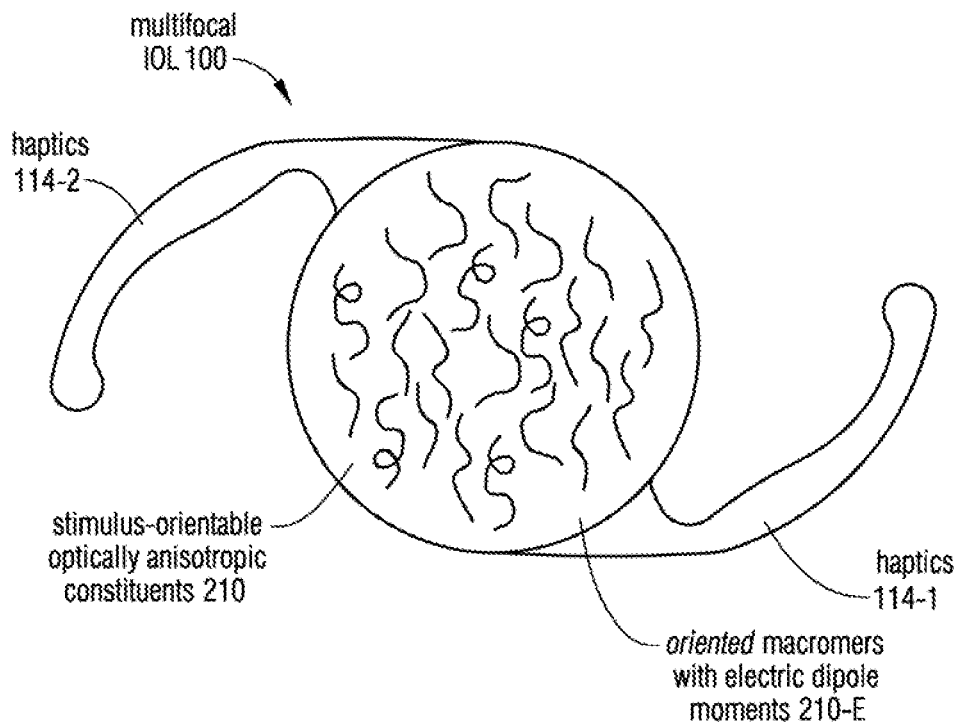

FIG. 5C shows the MF-IOL 100 after the stimulus 230 oriented the stimulus-orientable optically anisotropic constituents 210. In the shown example, this was carried out by the stimulus electric field 230-E orienting the macromers with electric dipole moment 210-E, and thus transforming the MF-IOL 100-po into an embodiment of the MF-IOL 100.

Figure 5D:
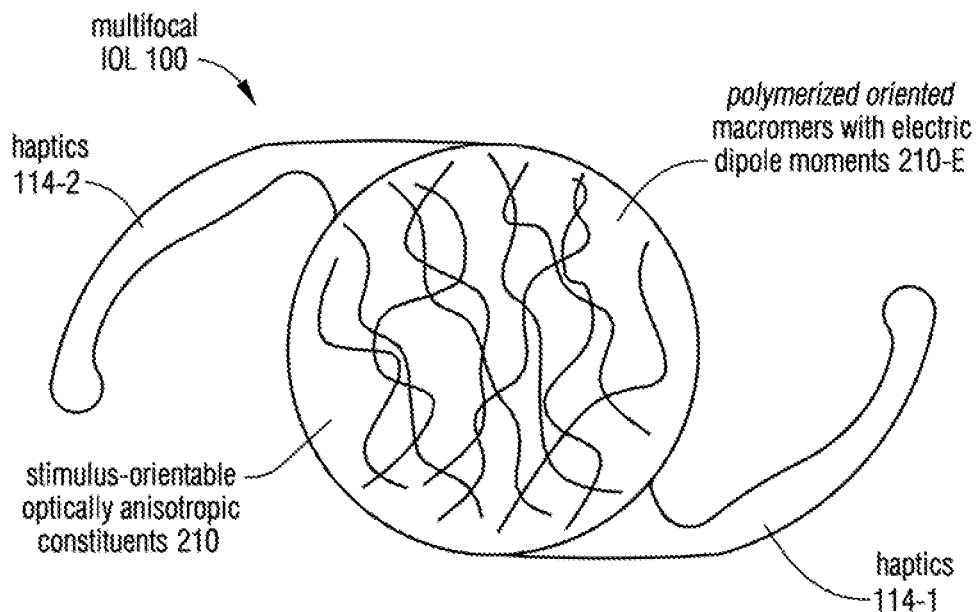

Finally, FIG. 5D illustrates that the fabrication of the MF-IOL 100 can proceed in general with polymerizing the oriented stimulus-orientable optically anisotropic constituents 210, in the specific example, by polymerizing the oriented macromers with electric dipole moments 210-E. Procedures other than polymerization can be also used to lock-in the macromers with electric dipole moments 210-E in their oriented state.

Figure 6A:
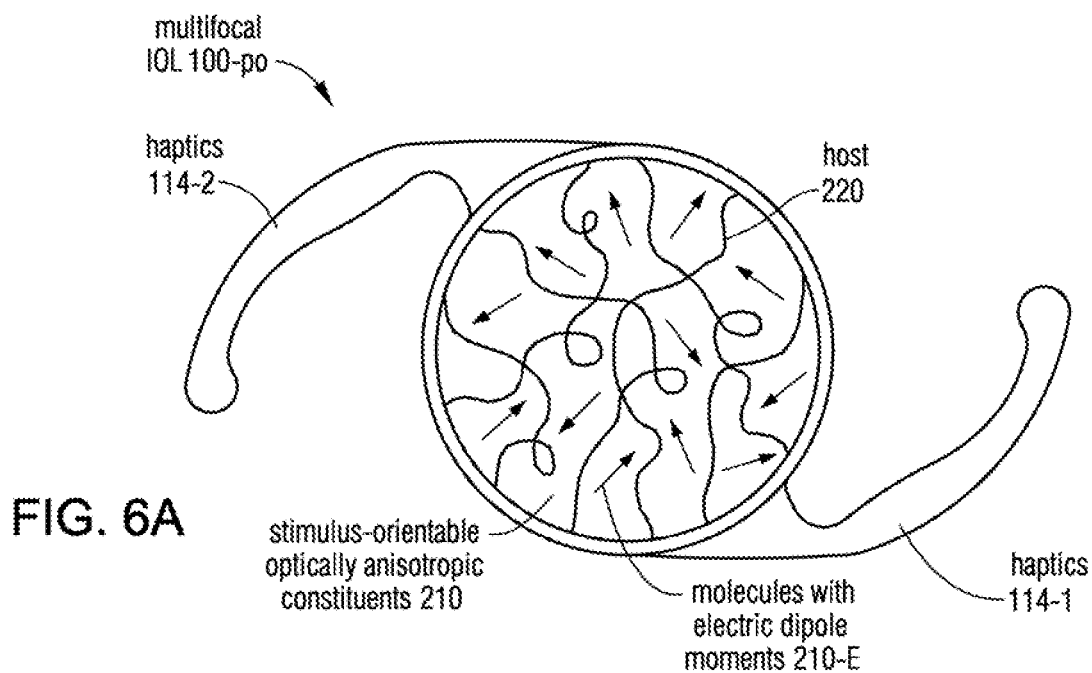
FIGS. 6A-C illustrate a multifocal IOL with stimulus-orientable optically anisotropic constituents such as molecules with electric dipole moments, before stimulus-induced orientation (FIG. 6A), the application of an orienting electric field stimulus (FIG. 6B), and the oriented optically anisotropic constituents after the application of the orienting electric field stimulus (FIG. 6C).
Figure 6B:
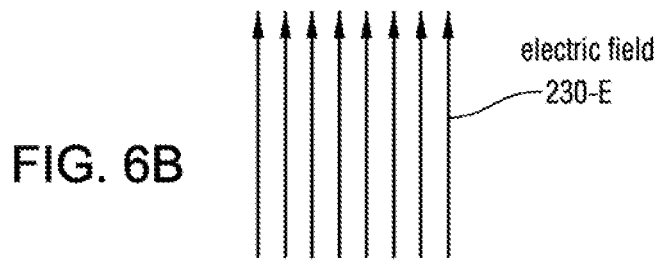
Figure 6C:
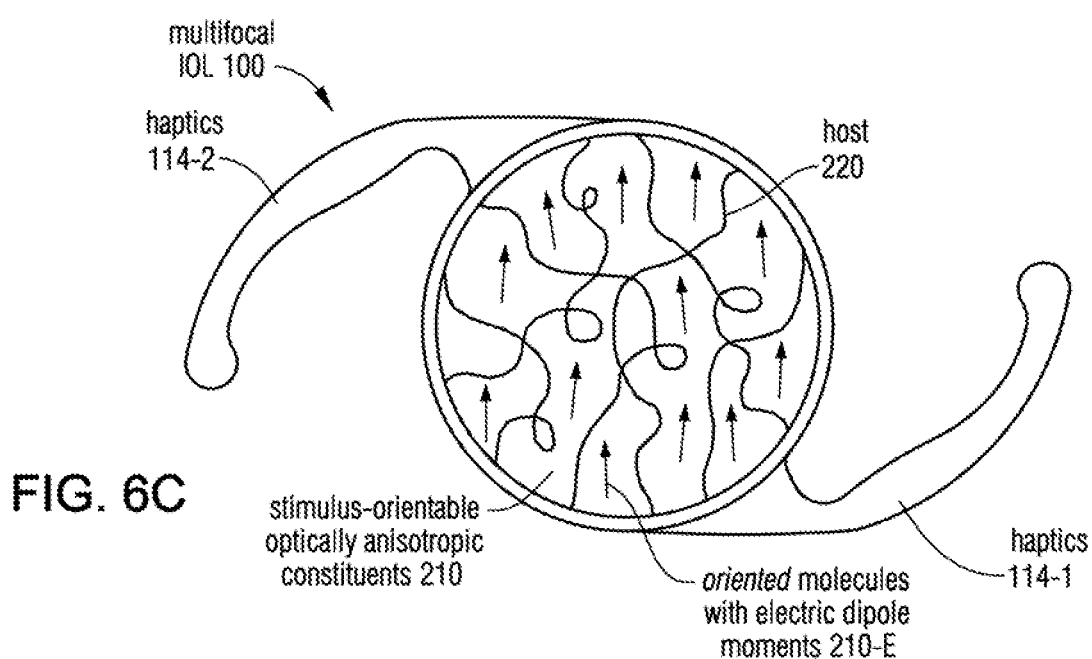

FIGS. 5A-D illustrated embodiments where the primary constituents of the MF-IOL 100 themselves were oriented by the stimulus 230. FIGS. 6A-C illustrate MF-IOLs 100 that include a host 220, or host matrix 220, to accommodate the stimulus-orientable optically anisotropic constituents 210. In such embodiments, the stimulus-orientable optically anisotropic constituents 210 can be oriented by the stimulus 230, while the host 220 itself is only moderately impacted by the stimulus 230, or not at all.

FIGS. 6A-C illustrate embodiments analogous to FIGS. 6A-D, where the stimulus-orientable optically anisotropic constituents 210 again have electric dipole moments 210-E.

FIG. 6A illustrates the MF-IOL 100-*po* with the stimulus-orientable optically anisotropic constituents 210 pointing in random directions "prior to orientation". There are many implementations of such stimulus-orientable optically anisotropic constituents having electric dipole moments 210-E, for example, nanowires, microwires, nanorods, nanotubes, anisotropic molecules, or elongated molecules. Each of them can have electric dipole moments and can be employed as a stimulus-orientable optically anisotropic constituent 210, such as an electric-field orientable constituent with an electric dipole moment 210-E. FIG. 6B illustrates symbolically the application of a stimulus 230, such as the stimulus electric field 230-E. Finally, FIG. 6C shows the MF-IOL 100 after the application of the stimulus electric field 230-E, with the molecules with electric dipole moments 210-E oriented by the stimulus electric field 230-E, thus having transformed the MF-IOL 100-*po* into an embodiment of the MF-IOL 100.

In other embodiments, the stimulus-orientable optically anisotropic constituents 210 can include polymer dispersed liquid crystals. Liquid crystals exhibit a strong response to the applied stimulus electric fields 230-E. Therefore, in MF-IOLs 100 where liquid crystals are part of the stimulus-orientable optically anisotropic constituents 210, a relatively large birefringence can be created with a relatively low electric field and voltage. The created birefringence is voltage- and concentration-dependent.

In analogy to FIG. 5D, in MF-IOLs 100 of FIGS. 6A-C, where the stimulus-orientable optically anisotropic constituents 210 are embedded in the host 220, the fabrication process can include a locking-in step, in order to lock-in the birefringence-creating oriented optically anisotropic constituents 210 in their oriented state, generated by the stimulus 230. In cases, when the locking-in is performed before implanting the MF-IOL 100 into the eye, it can involve polymerizing the MF-IOL 100, to freeze the oriented stimulus-orientable optically anisotropic constituents 210 in their oriented state, fusing them together with the host 220.

Figure 7A:
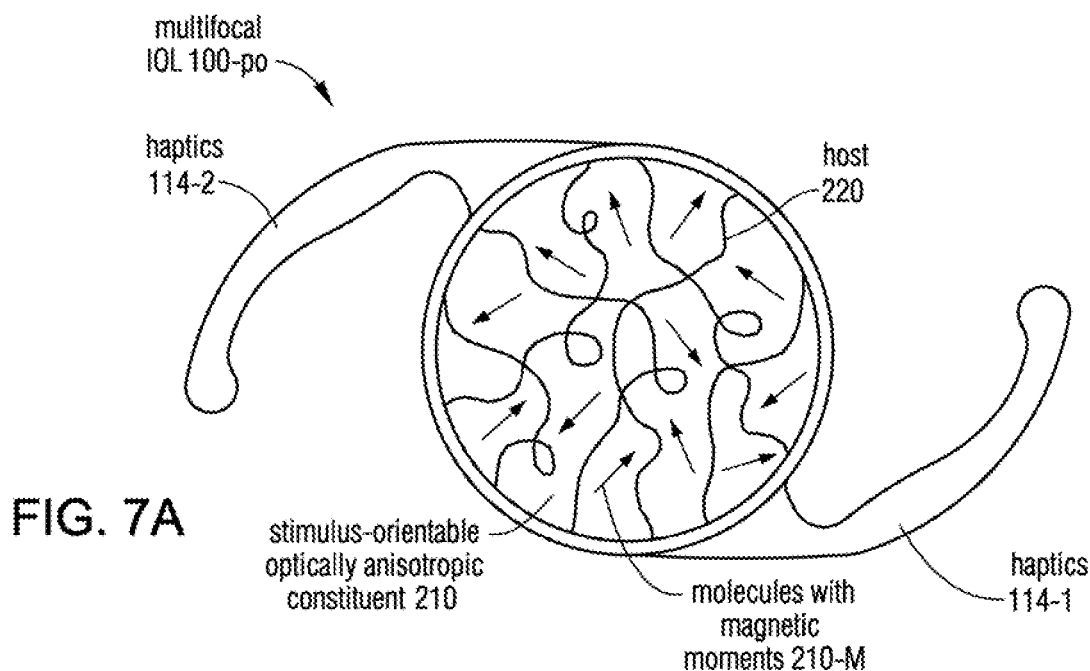
FIGS. 7A-C illustrate a multifocal IOL with stimulus-orientable optically anisotropic constituents such as molecules with magnetic moments, before a stimulus-induced orientation (FIG. 7A), the application of an orienting magnetic field stimulus (FIG. 7B), and the oriented optically anisotropic constituents after the application of the orienting magnetic field stimulus (FIG. 7C).
Figure 7B:
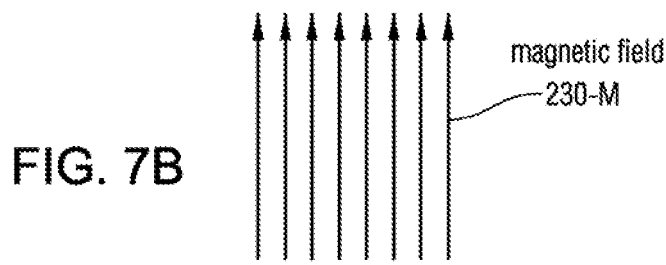
Figure 7C:
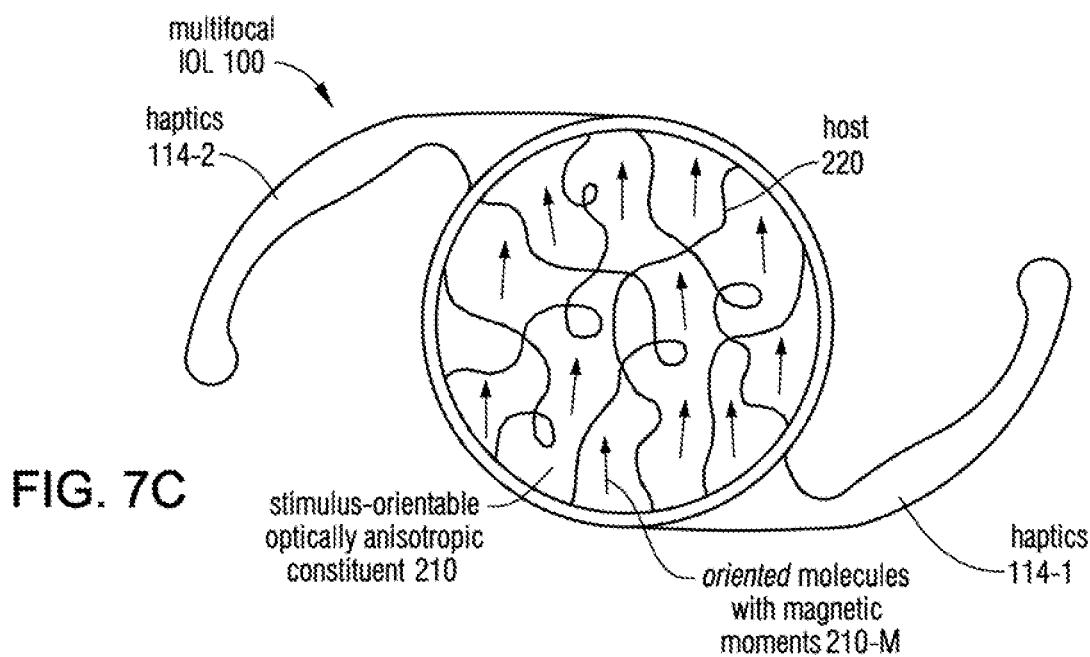

In other embodiments of the MF-IOL 100, the stimulus-orientable optically anisotropic constituents 210 can be stimulus-orientable by a magnetic field, a temperature gradient, or a chemical gradient. FIGS. 7A-C illustrate a corresponding example, where a magnetic field provides the stimulus 230. FIG. 7A shows an embodiment of the MF-IOL 100-*po* where the stimulus-orientable optically anisotropic constituents 210 include molecules with magnetic moments 210-M, embedded into the host 220, prior to orientation. FIG. 7B illustrates that the stimulus 230 can be an application of a magnetic field 230-M. Finally, FIG. 7C illustrates that the stimulus 230-M by the magnetic field oriented the molecules with magnetic moments 210-M, thus transforming the MF-IOL 100-*po* in an embodiment of the MF-IOL 100. As before, the orientation of these molecules with magnetic moments 210-M needs to be locked in to a suitable degree before or after the implantation of the MF-IOL 100 into the eye.

In some implementations of the MF-IOL 100, the stimulus-orientable optically anisotropic constituents 210 are stimulus-orientable by illumination with at least one of a linearly polarized light and a circularly polarized light as the stimulus 230. In MF-IOLs 100, in which the stimulus-orientable optically anisotropic constituents 210 can be oriented by the magnetic field 230-M, or by the now described polarized lights, the birefringence of the MF-IOL 100 can be induced in vivo, after the implantation of the MF-IOL 100 into the eye.

Such embodiments offer a genuinely new medical advantage, as IOLs often rotate or shift after the implantation. Good visual acuity is achieved if the extended depth of focus EDOF covers a depth range with the retina 5 optimally located in this depth range, typically centrally. If, however, the MF-IOL 100 shifts after the implantation, the depth range of the EDOF may shift relative to the retina 5, possibly even to a degree that the retina 5 falls completely outside the optimal depth range. In such cases, the MF-IOL 100 may deliver a Visual Acuity substantially inferior compared to the expectations. This challenge can be managed by the here-described MF-IOLs 100, where the EDOF depth range can be formed in vivo, after the implanted MF-IOL 100 settled in the capsule. Performing the lock-in step in vivo can ensure that the depth range of the EDOF encompasses the retina 5 according to the pre-surgical planning. Similar medical benefits and improvements can be achieved in the context of the MF-IOL 100 rotating after implantation. Applying the stimulus 230 in vivo, in the settled MF-IOL 100, can make sure that the polarization planes are oriented according to the pre-surgical planning.

One class of examples is MF-IOLs 100 where the stimulus-orientable optically anisotropic constituents 210 are liquid crystals, often embedded into a polymer host 220. Some liquid crystals exhibit an effect called "Giant Optical Nonlinearity": they increasingly align with the polarization plane of the light stimulus 230, as the intensity of the light increases. Such Giant Optical Nonlinearity-exhibiting liquid crystals can be used in MF-IOLs 100 as the stimulus-orientable optically anisotropic constituents 210 to be oriented in vivo via the stimulus 230 by a polarized light. As before, a subsequent lock-in step may be helpful to lock-in the oriented liquid crystal constituents 210.

The light delivery systems like the ones described in co-pending, commonly owned U.S. patent application U.S. Ser. No. 15/159,909, entitled "Method for modifying power of light adjustable lens" by R. Grubbs and C. Sandstedt, hereby incorporated in its entirety by reference, can be adapted and programmed to polarize the illuminating light with a predetermined polarization and intensity profile to deliver the here-described polarized light stimulus 230. The light delivery system can illuminate the implanted MF-IOL 100 with this polarized light stimulus 230 after the MF-IOL 100 settled in the capsule, to form an embodiment of the MF-IOL 100 in vivo.

In some embodiments, the post-implantation, in vivo stimulus 230 can be applied by a magnetic field 230-M. The corresponding MF-IOLs 100 can include molecules with magnetic moments 210-M to be responsive to this in vivo magnetic field stimulus 230-M.

In some embodiments of the MF-IOL 100, the stimulus-orientable optically anisotropic constituents 210 can be stimulus-orientable by a non-stretching stimulus. Stretching may be applied to an IOL material in large sheets by machinery to mechanically urge constituents of the IOL to orient. However, modern IOLs are typically fabricated in individual molds instead of large sheets, where several fabrication steps are performed that involve heating, shaping, and chemical reactions. All these steps can undermine and reduce the birefringence induced by a prior stretching. And in reverse, if the stretching step is performed at the end of the fabrication process, the optical performance, clarity, and precision of the IOL can be negatively impacted. For all these reasons, fabricating the MF-IOLs 100 with the above described, non-stretching stimuli 230 can deliver distinctly superior performance and is better suited for modern fabrication methods.

Figure 8A:
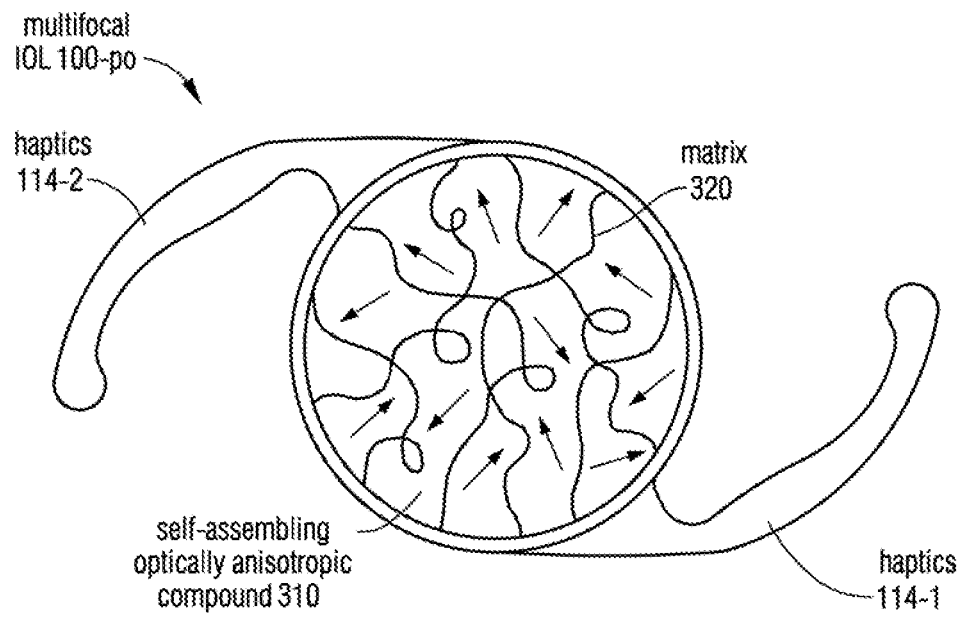
FIGS. 8A-B illustrate a birefringent multifocal IOL with self-assembling optically anisotropic compounds before self-assembly (FIG. 8A), and after oriented self-assembly (FIG. 8B).
Figure 8B:
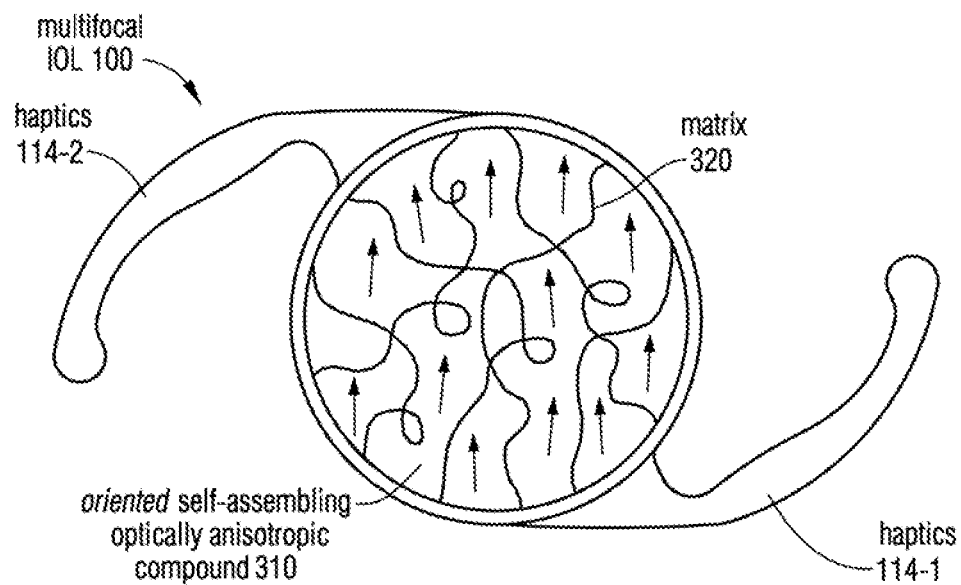

FIGS. 8A-B illustrate an embodiment of the MF-IOL 100 that includes a self-assembling optically anisotropic compound 310; adapted to modify the MF-IOL 100 to have an ordinary index of refraction $n_o$ for an ordinary light component; an extraordinary index of refraction $n_e$ for an extraordinary light component; an ordinary optical power $D_o$ for the ordinary light component; and an extraordinary optical power $D_e$ for the extraordinary light component, wherein $D_e/D_o=(n_e-1)/(n_o-1)$; and haptics 114, to position the multifocal intraocular lens 100 inside an eye.

In some embodiments, the self-assembling optically anisotropic compound 310 can include amphiphilic molecules, lipids, surfactants, nanostructures, or liquid crystals. FIG. 8A illustrates an embodiment of the MF-IOL 100-po prior to orientation, where the self-assembling optically anisotropic compound 310 can be embedded into a matrix 320 without a prior orientation. FIG. 8B illustrates that the constituents of this self-assembling optically anisotropic compound 310 can align and orient themselves as part of the fabrication process, without a stimulus of the type of 130 or 230. This tendency for self-assembly can be driven by a variety of forces and factors, including hydrophobia, hydrophilicity, electric forces, dipolar torques, and van der Walls forces, among others. Moreover, the self-assembling tendencies of the constituents of the compound 310 can be strong enough to lock-in themselves in the aligned and oriented state. Thus, in some MF-IOLs 100 with a self-assembling optically anisotropic compound 310, there is no need for a subsequent lock-in step. This feature can be quite helpful and simplifying for the MF-IOLs 100.

Figure 9:
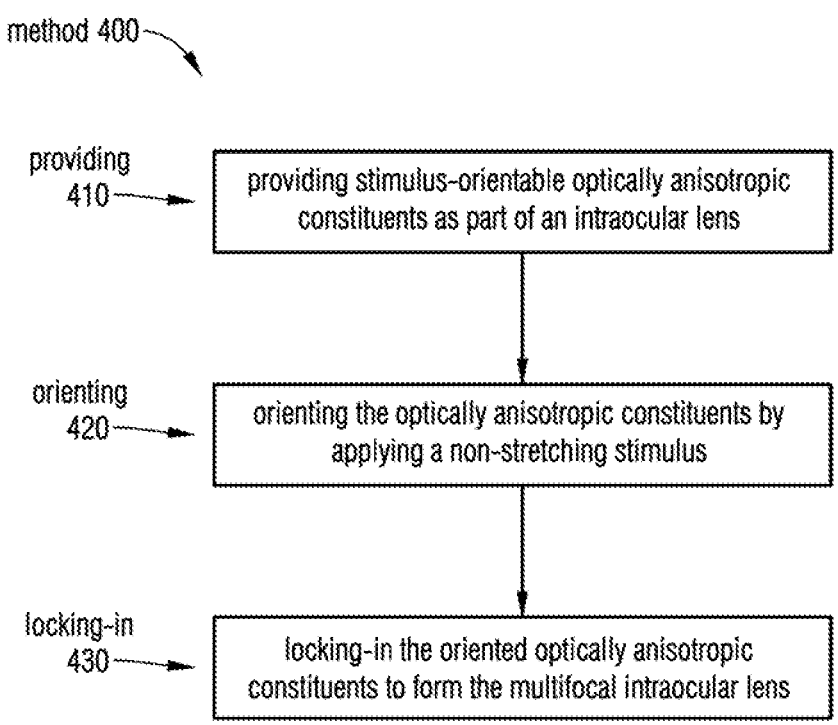
FIG. 9 illustrates a method of making a multifocal intraocular lens.

FIG. 9 illustrates a method 400 for the making or the fabrication of a multifocal intraocular lens 100. The method 400 can include the following steps.

providing stimulus-orientable optically anisotropic constituents as part of an intraocular lens, in a providing 410 step;

orienting the optically anisotropic constituents by applying a non-stretching stimulus, in an orienting step 420; and locking-in the oriented optically anisotropic constituents to form the multifocal intraocular lens, in a locking-in step 430.

In some embodiments, as mentioned in relation to applying the stimulus 130 and 230, the applying the non-stretching stimulus in the orienting step 420 can include applying an electric field, a magnetic field, a thermal gradient, or a chemical gradient to the intraocular lens.

In some embodiments, as mentioned in relation to applying the stimulus 130 and 230, the applying the non-stretching stimulus in the orienting step 420 can include illuminating the intraocular lens with at least one of a linearly polarized light and a circularly polarized light.

As mentioned in the context of FIG. 5D and other embodiments, the locking-in step 430 can include polymerizing the oriented optically anisotropic constituents 210 before implanting the multifocal intraocular lens 100 into an eye.

As mentioned before in the context of FIG. 5D and other embodiments, the locking-in step 430 can include locking-in the oriented optically anisotropic constituents 210 after implanting the multifocal intraocular lens into an eye.

Although embodiments of the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and/or steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A multifocal intraocular lens, comprising:
a stimulus-adjustable circularly birefringent material with a right-handed index of refraction $n_R$ for a light with a right-handed polarization, and a left-handed index of refraction $n_L$ for a light with a left-handed polarization; and haptics, to position the multifocal intraocular lens inside a capsule of an eye; wherein the multifocal intraocular lens has a right-handed optical power $D_R$ for the light with the right-handed polarization, and a left-handed optical power $D_L$ for the light with the left-handed polarization, wherein $D_L/D_R=(n_L-1)/(n_R-1);$ and the birefringent material has a composition that makes it possible to lock in the stimulus adjustment irreversibly, and includes chiral molecules, embedded into a matrix.

2. The multifocal intraocular lens of claim 1, the matrix comprising:
at least one of monomers, macromers, and polymers.

3. The multifocal intraocular lens of claim 1, wherein:
the chiral molecules are spatially aligned.

4. The multifocal intraocular lens of claim 1, wherein:
the chiral molecules include at least one of a DNA, an optically active isomer of a sugar, a liquid crystal, a cholesterol, a cholesteric liquid crystal, and a chiral molecule with circular birefringence.

5. A multifocal intraocular lens, comprising:
a stimulus-adjustable circularly birefringent material with a right-handed index of refraction $n_R$ for a light with a right-handed polarization, and a left-handed index of refraction $n_L$ for a light with a left-handed polarization; and haptics, to position the multifocal intraocular lens inside a capsule of an eye; wherein the multifocal intraocular lens has a right-handed optical power $D_R$ for the light with the right-handed polarization, and a left-handed optical power $D_L$ for the light with the left-handed polarization, wherein $D_L/D_R=(n_L-1)/(n_R-1);$ the birefringent material has a composition that makes it possible to lock in the stimulus adjustment irreversibly; and the stimulus adjustable circularly birefringent material is adjustable by at least one of an application of an electric field, a magnetic field, a chemical gradient, a temperature gradient, and an illumination with at least one of a linearly polarized light and a circularly polarized light.

* * * * *